United States Patent
Vail et al.

(10) Patent No.: US 9,700,544 B2
(45) Date of Patent: Jul. 11, 2017

(54) ORAL RAPAMYCIN NANOPARTICLE PREPARATIONS

(71) Applicants: Neal K Vail, Castle Hills, TX (US); Dana M Vaughn, Seguin, TX (US)

(72) Inventors: Neal K Vail, Castle Hills, TX (US); Dana M Vaughn, Seguin, TX (US)

( * ) Notice: Subject to any disclaimer, the term of this patent is extended or adjusted under 35 U.S.C. 154(b) by 0 days.

(21) Appl. No.: 14/221,137

(22) Filed: Mar. 20, 2014

(65) Prior Publication Data

US 2015/0202164 A1   Jul. 23, 2015

Related U.S. Application Data

(60) Provisional application No. 61/922,800, filed on Dec. 31, 2013.

(51) Int. Cl.
*A61K 31/436* (2006.01)
*A61K 9/16* (2006.01)
*A61K 9/51* (2006.01)

(52) U.S. Cl.
CPC .......... *A61K 31/436* (2013.01); *A61K 9/1635* (2013.01); *A61K 9/5123* (2013.01); *A61K 9/5146* (2013.01)

(58) Field of Classification Search
None
See application file for complete search history.

(56) References Cited

U.S. PATENT DOCUMENTS

| | | | |
|---|---|---|---|
| 716,067 A | 12/1902 | Lemon et al. | |
| 3,929,992 A | 12/1975 | Sehgal et al. | |
| 3,993,749 A | 11/1976 | Sehgal et al. | |
| 4,316,885 A | 2/1982 | Rakhit | |
| 4,401,653 A | 8/1983 | Eng | |
| 4,460,722 A | 7/1984 | Igarashi et al. | |
| 4,885,171 A | 12/1989 | Surendra et al. | |
| 5,023,262 A | 6/1991 | Caufield et al. | |
| 5,023,263 A | 6/1991 | Burg | |

(Continued)

FOREIGN PATENT DOCUMENTS

| | | |
|---|---|---|
| CA | 2572100 A1 | 6/2007 |
| EP | 778023 A | 6/1997 |

(Continued)

OTHER PUBLICATIONS

"Sirolimus," Wikipedia website located at http://en.wikipedia.org/wiki/Rapamycin, downloaded Oct. 20, 2009.

(Continued)

*Primary Examiner* — Carlos Azpuru
*Assistant Examiner* — Casey Hagopian
(74) *Attorney, Agent, or Firm* — William H. Quirk; Jesse Frizzell; Rosenthal Pauerstein Sandoloski Agather LLP

(57) ABSTRACT

Oral preparations of microcapsules and nanoparticles including an inhibitor of the mammalian target of rapamycin. The preparations are intended to assist with the treatment and prevention of cancer neurocognitive dysfunction, genetically predisposed disorders, and age-related disorders. The embodiments discussed address the present need for alternative preparations or manufacturing processes that ensure efficacy while improving other performance characteristics such as storage stability, biodistribution, dosage cost, etc.

15 Claims, 4 Drawing Sheets

(56) References Cited

U.S. PATENT DOCUMENTS

| | | |
|---|---|---|
| 5,023,264 A | 6/1991 | Caufield et al. |
| 5,066,493 A | 11/1991 | Sehgal et al. |
| 5,078,999 A | 1/1992 | Warner et al. |
| 5,080,899 A | 1/1992 | Sturm et al. |
| 5,100,883 A | 3/1992 | Schiehser |
| 5,100,899 A | 3/1992 | Calne |
| 5,102,876 A | 4/1992 | Caufield |
| 5,118,677 A | 6/1992 | Caufield |
| 5,118,678 A | 6/1992 | Kao et al. |
| 5,120,725 A | 6/1992 | Kao et al. |
| 5,120,726 A | 6/1992 | Failli et al. |
| 5,120,727 A | 6/1992 | Kao et al. |
| 5,120,842 A | 6/1992 | Failli et al. |
| 5,130,307 A | 7/1992 | Failli et al. |
| 5,138,051 A | 8/1992 | Hughes et al. |
| 5,151,413 A | 9/1992 | Caufield et al. |
| 5,162,333 A | 11/1992 | Failli et al. |
| 5,164,399 A | 11/1992 | Failli et al. |
| 5,169,851 A | 12/1992 | Hughes et al. |
| 5,177,203 A | 1/1993 | Failli et al. |
| 5,194,447 A | 3/1993 | Kao |
| 5,202,332 A | 4/1993 | Hughes et al. |
| 5,206,018 A | 4/1993 | Sehgal et al. |
| 5,221,670 A | 6/1993 | Caufield |
| 5,221,740 A | 6/1993 | Hughes |
| 5,233,036 A | 8/1993 | Hughes |
| 5,260,299 A | 11/1993 | Failli et al. |
| 5,260,300 A | 11/1993 | Hu |
| 5,262,423 A | 11/1993 | Kao |
| 5,262,424 A | 11/1993 | Kao |
| 5,286,731 A | 2/1994 | Caufield et al. |
| 5,288,711 A | 2/1994 | Mitchell et al. |
| 5,302,584 A | 4/1994 | Kao et al. |
| 5,310,903 A | 5/1994 | Goulet et al. |
| 5,321,009 A | 6/1994 | Baeder et al. |
| 5,344,833 A | 9/1994 | Hughes |
| 5,346,893 A | 9/1994 | Failli et al. |
| 5,358,944 A | 10/1994 | Caufield |
| 5,362,718 A | 11/1994 | Skotnicki et al. |
| 5,373,014 A | 12/1994 | Failli et al. |
| 5,378,696 A | 1/1995 | Caufield |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,411,967 A | 5/1995 | Kao et al. |
| 5,434,260 A | 7/1995 | Skotnicki et al. |
| 5,446,048 A | 8/1995 | Failli et al. |
| 5,463,048 A | 10/1995 | Skotnicki et al. |
| 5,480,988 A | 1/1996 | Failli et al. |
| 5,480,989 A | 1/1996 | Kao et al. |
| 5,484,790 A | 1/1996 | Failli et al. |
| 5,484,791 A | 1/1996 | Failli et al. |
| 5,486,522 A | 1/1996 | Failli et al. |
| 5,486,523 A | 1/1996 | Failli et al. |
| 5,486,524 A | 1/1996 | Failli et al. |
| 5,488,054 A | 1/1996 | Failli et al. |
| 5,489,595 A | 2/1996 | Failli et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,504,204 A | 4/1996 | Failli et al. |
| 5,504,291 A | 4/1996 | Goble et al. |
| 5,508,285 A | 4/1996 | Nelson et al. |
| 5,508,286 A | 4/1996 | Skotnicki et al. |
| 5,508,290 A | 4/1996 | Nelson et al. |
| 5,508,399 A | 4/1996 | Kao et al. |
| 5,516,780 A | 5/1996 | Skotnicki et al. |
| 5,519,031 A | 5/1996 | Skotnicki et al. |
| 5,521,194 A | 5/1996 | Nelson et al. |
| 5,525,610 A | 6/1996 | Caufield et al. |
| 5,530,007 A | 6/1996 | Kao et al. |
| 5,530,121 A | 6/1996 | Kao et al. |
| 5,532,355 A | 7/1996 | Skotnicki et al. |
| 5,536,729 A | 7/1996 | Waranis et al. |
| 5,541,191 A | 7/1996 | Skotnicki et al. |
| 5,541,192 A | 7/1996 | Skotnicki et al. |
| 5,550,133 A | 8/1996 | Failli et al. |
| 5,552,160 A | 9/1996 | Liversidge et al. |
| 5,559,112 A | 9/1996 | Skotnicki et al. |
| 5,559,119 A | 9/1996 | Skotnicki et al. |
| 5,559,120 A | 9/1996 | Kao et al. |
| 5,559,121 A | 9/1996 | Harrison et al. |
| 5,559,122 A | 9/1996 | Nelson et al. |
| 5,561,138 A | 10/1996 | Armstrong |
| 5,563,145 A | 10/1996 | Failli et al. |
| 5,567,709 A | 10/1996 | Skotnicki et al. |
| 5,637,590 A | 6/1997 | Skotnicki et al. |
| 5,665,772 A | 9/1997 | Cottens et al. |
| 5,780,462 A | 7/1998 | Lee et al. |
| 5,891,469 A | 4/1999 | Amselem |
| 5,912,253 A | 6/1999 | Cottens et al. |
| 5,922,730 A | 7/1999 | Hu et al. |
| 5,932,243 A | 8/1999 | Fricker et al. |
| 5,955,457 A | 9/1999 | Lee et al. |
| 5,985,890 A | 11/1999 | Cottens et al. |
| 5,989,591 A | 11/1999 | Nagi |
| 6,004,973 A | 12/1999 | Guitard et al. |
| 6,015,809 A | 1/2000 | Zhu et al. |
| 6,197,781 B1 | 3/2001 | Guitard et al. |
| 6,200,985 B1 | 3/2001 | Cottens et al. |
| 6,204,243 B1 | 3/2001 | Posanski |
| 6,228,396 B1 | 5/2001 | Watts |
| RE37,421 E | 10/2001 | Holt et al. |
| 6,329,386 B1 | 12/2001 | Mollison |
| 6,386,869 B1 * | 5/2002 | Zegarelli ................... 433/80 |
| 6,399,625 B1 | 6/2002 | Zhu |
| 6,440,990 B1 | 8/2002 | Cottens et al. |
| 6,475,518 B1 | 11/2002 | Baumgart et al. |
| 6,486,099 B2 | 11/2002 | Igari et al. |
| 6,503,883 B1 | 1/2003 | Posanski |
| 6,537,195 B2 | 3/2003 | Forman |
| 6,555,132 B1 | 4/2003 | Brox et al. |
| 6,569,463 B2 | 5/2003 | Patel et al. |
| 6,592,916 B2 | 7/2003 | Soeda et al. |
| 6,596,268 B1 | 7/2003 | Coffey et al. |
| 6,605,298 B1 | 8/2003 | Leigh et al. |
| 6,649,157 B2 | 11/2003 | Coffey et al. |
| 6,653,256 B1 | 11/2003 | Wolf |
| 6,670,355 B2 | 12/2003 | Azrolan et al. |
| 6,677,357 B2 | 1/2004 | Zhu et al. |
| 6,680,330 B2 | 1/2004 | Zhu et al. |
| 6,923,988 B2 | 8/2005 | Patel et al. |
| 6,929,818 B2 | 8/2005 | Luthra et al. |
| 6,936,644 B2 | 8/2005 | Gilleo |
| 6,956,043 B2 | 10/2005 | Guitard et al. |
| 6,974,473 B2 | 12/2005 | Barclay et al. |
| 7,008,979 B2 | 3/2006 | Schottman et al. |
| 7,037,582 B2 | 5/2006 | Xing et al. |
| 7,041,046 B2 | 5/2006 | Forman |
| 7,041,283 B1 * | 5/2006 | Achim et al. ................ 424/93.1 |
| 7,084,171 B2 | 8/2006 | Grainger et al. |
| 7,132,458 B2 | 11/2006 | Burton et al. |
| 7,160,867 B2 | 1/2007 | Abel et al. |
| 7,220,755 B2 | 5/2007 | Betts et al. |
| 7,241,771 B2 | 7/2007 | Zhu |
| 7,268,144 B2 | 9/2007 | Gu et al. |
| 7,271,177 B2 | 9/2007 | Benjamin et al. |
| 7,273,874 B2 | 9/2007 | Graziani et al. |
| 7,276,498 B2 | 10/2007 | Graziani et al. |
| 7,279,562 B2 | 10/2007 | Molnar-Kimber et al. |
| 7,282,505 B2 | 10/2007 | Zhu et al. |
| 7,292,885 B2 | 11/2007 | Scott et al. |
| 7,304,033 B2 | 12/2007 | Larsen et al. |
| 7,345,053 B2 | 3/2008 | Garvey |
| 7,445,916 B2 | 11/2008 | Gu et al. |
| 7,446,111 B2 | 11/2008 | Benjamin et al. |
| 7,452,723 B2 | 11/2008 | Coffey et al. |
| 7,455,853 B2 | 11/2008 | Mollison et al. |
| 7,470,682 B2 | 12/2008 | Graziani et al. |
| 7,476,678 B2 | 1/2009 | Graziani et al. |
| 7,488,444 B2 | 2/2009 | Furst et al. |

(56) References Cited

U.S. PATENT DOCUMENTS

| | | | |
|---|---|---|---|
| 7,517,342 | B2 | 4/2009 | Scott et al. |
| 7,517,362 | B2 | 4/2009 | Shanley et al. |
| 7,519,418 | B2 | 4/2009 | Scott et al. |
| 7,538,119 | B2 | 5/2009 | Gu et al. |
| 7,541,380 | B2 * | 6/2009 | Bianchi et al. ............... 514/433 |
| 7,560,457 | B2 | 7/2009 | Graziani et al. |
| 7,576,903 | B2 | 8/2009 | Yamamoto et al. |
| 7,763,271 | B1 * | 7/2010 | Ding ...................... A61L 31/10 424/422 |
| 8,007,831 | B2 | 8/2011 | Lewis et al. |
| 8,053,444 | B2 | 11/2011 | Reven et al. |
| 8,343,926 | B2 | 1/2013 | Nagy |
| 2001/0026807 | A1 | 10/2001 | Watts |
| 2002/0009473 | A1 | 1/2002 | Tebbe |
| 2003/0176455 | A1 | 9/2003 | Adelman |
| 2003/0215496 | A1 | 11/2003 | Patel et al. |
| 2004/0010002 | A1 | 1/2004 | Wasik et al. |
| 2004/0074089 | A1 | 4/2004 | Gilleo |
| 2004/0121155 | A1 | 6/2004 | Matsunami et al. |
| 2005/0090553 | A1 | 4/2005 | Shapiro |
| 2005/0113282 | A1 | 5/2005 | Parekh et al. |
| 2006/0115533 | A1 | 6/2006 | Guitard et al. |
| 2006/0121122 | A1 | 6/2006 | Nakajima et al. |
| 2006/0210638 | A1 | 9/2006 | Liversidge et al. |
| 2006/0234053 | A1 | 10/2006 | Yamamoto et al. |
| 2006/0251710 | A1 * | 11/2006 | Kwon et al. ................. 424/450 |
| 2006/0251720 | A1 | 11/2006 | Penhasi et al. |
| 2006/0264453 | A1 | 11/2006 | Mudumba et al. |
| 2007/0082829 | A1 | 4/2007 | Smets et al. |
| 2007/0138673 | A1 | 6/2007 | Lee et al. |
| 2007/0142423 | A1 | 6/2007 | Graziani et al. |
| 2007/0185150 | A1 | 8/2007 | Bedrosian |
| 2007/0203168 | A1 | 8/2007 | Zhao |
| 2007/0203169 | A1 | 8/2007 | Zhao |
| 2007/0203170 | A1 | 8/2007 | Zhao |
| 2007/0203171 | A1 | 8/2007 | Zhao |
| 2007/0203172 | A1 | 8/2007 | Zhao |
| 2007/0225313 | A1 | 9/2007 | Zhao |
| 2007/0280992 | A1 * | 12/2007 | Margaron et al. ............ 424/426 |
| 2008/0022965 | A1 | 1/2008 | Bysveen et al. |
| 2008/0069797 | A1 | 3/2008 | Roncarolo et al. |
| 2008/0085880 | A1 | 4/2008 | Viswanath et al. |
| 2008/0091008 | A1 | 4/2008 | Viswanath et al. |
| 2008/0138405 | A1 | 6/2008 | Raheja et al. |
| 2008/0182867 | A9 | 7/2008 | Wasik et al. |
| 2008/0188511 | A1 | 8/2008 | Beckmann et al. |
| 2008/0193653 | A1 | 8/2008 | Oh |
| 2008/0214595 | A1 | 9/2008 | Izumo et al. |
| 2008/0234380 | A1 | 9/2008 | Shapiro |
| 2008/0249123 | A1 | 10/2008 | Gu et al. |
| 2008/0275076 | A1 | 11/2008 | Holm et al. |
| 2010/0105696 | A1 | 4/2010 | Garcia-Echeverria et al. |
| 2010/0150864 | A1 | 6/2010 | Hickman et al. |
| 2010/0303901 | A1 * | 12/2010 | Shimoni .............. A61K 9/1617 424/455 |
| 2011/0104256 | A1 | 5/2011 | Wang et al. |
| 2011/0105387 | A1 | 5/2011 | Wu et al. |
| 2011/0195966 | A1 | 8/2011 | Garcia-Echeverria et al. |
| 2011/0293731 | A1 | 12/2011 | Lewis et al. |
| 2012/0064143 | A1 * | 3/2012 | Sharp .................. A61K 9/1635 424/439 |
| 2012/0122913 | A1 | 5/2012 | Charbonneau et al. |
| 2012/0276169 | A1 | 11/2012 | Kang et al. |

FOREIGN PATENT DOCUMENTS

| | | |
|---|---|---|
| EP | 1393747 A1 | 3/2004 |
| EP | 1709974 A2 | 10/2006 |
| EP | 2322163 A1 | 5/2011 |
| WO | 9531194 A1 | 11/1995 |
| WO | 0197809 A2 | 12/2001 |
| WO | 2005034916 A1 | 4/2005 |
| WO | 2007093346 A1 | 8/2007 |
| WO | 2008022256 A2 | 2/2008 |
| WO | 2010022243 A1 | 8/2009 |
| WO | 2009133141 A2 | 11/2009 |
| WO | 2009133142 A1 | 11/2009 |
| WO | 2010056754 A3 | 5/2010 |
| WO | 2011009193 A1 | 1/2011 |
| WO | 2014059295 A1 | 4/2014 |
| WO | 2014144346 A1 | 9/2014 |
| WO | 2014144405 A1 | 9/2014 |

OTHER PUBLICATIONS

Aguilar et al., "S6 kinase deletion suppresses muscle growth adaptations to nutrient availabilityby activating AMP kinase," Cell Metab, 5:476-487, 2007.

An et al., "Mechanism of zinc-induced phosphorylation of p70 S6 kinase and glycogensynthase kinase 3beta in SH-SY5Y neuroblastoma cells," J Neurochem. Mar. 2005;92(5):1104-15.

An et al., "Up-regulation of phosphorylated/activated p70 S6 kinase and its relationship toneurofibrillary pathology in Alzheimer's disease," Am J Pathol. Aug. 2003;163(2):591-607.Erratum in: Am J Pathol. Dec. 2003;163(6):2645.

Balan et al., "Life span extension and neuronal cell protection by *Drosophila nicotinamidase*," JBiol Chem. Oct. 10, 2008;283(41):27810-9.

Banko et al., "The translation repressor 4E-BP2 is critical for eIF4F complex formation,synaptic plasticity, and memory in the hippocampus," J. Neurosci., 25:9581-9590, 2005.

Bayes et al., "Gateways to clinical trials," Methods Find Exp Clin Pharmacol. Dec. 2006;28(10):719-40.

Benhamou, "Immunomodulation with CTLA4-Ig in islet transplantation," Transplantation.Jan. 15, 2002;73(1 Suppl): S40-2.

Bhaskar et al., "The PI3K-Akt-mTOR pathway regulates Abeta oligomer induced neuronal cellcycle events," Mol Neurodegener. Mar. 16, 2009;4:14.

Billings et al., "Intraneuronal Abeta causes the onset of early Alzheimer's disease-relatedcognitive deficits in transgenic mice," Neuron, 45:675-688, 2005.

Bisht et al., "In vivo characterization of a polymeric nanoparticle platform with potential oraldrug delivery capabilities," Mol Cancer Ther. Dec. 2008;7(12):3878-88.

Björkdahl et al., "Zinc induces neurofilament phosphorylation independent of p70 S6 kinase inN2a cells," Neuroreport. Apr. 25, 2005;16(6):591-5.

Blagosklonny, "Aging and immortality: quasi-programmed senescence and its pharmacologicinhibition," Cell Cycle. Sep. 2006;5(18):2087-102.

Blagosklonny, "An anti-aging drug today: from senescence-promoting genes to anti-aging pill," Drug Discov Today. Mar. 2007;12(5-6):218-24.

Blagosklonny, "Paradoxes of aging," Cell Cycle. Dec. 15, 2007;6(24):2997-3003.

Boland et al., "Autophagy induction and autophagosome clearance in neurons: relationship toautophagic pathology in Alzheimer's disease," J Neurosci. Jul. 2, 2008;28(27):6926-37.

Caccamo et all' "Rapamycin rescues TDP-43 mislocalization and the associated low molecularmass neurofilament instability," J Biol Chem. Oct. 2, 2009;284(40):27416-24.

Cao et al., "Toll-like receptor-mediated induction of type I interferon in plasmacytoid dendriticcells requires the rapamycin-sensitive PI(3)K-mTOR-p70S6K pathway," Nat Immunol. Oct. 2008;9(10):1157-64.

Carlson et al., "Perinatal iron deficiency results in altered developmental expression of genesmediating energy metabolism and neuronal morphogenesis in hippocampus," Hippocampus2007;17(8):679-91.

Carter et al., "Molecular mechanisms of life- and health-span extension: role of calorierestriction and exercise intervention," Appl Physiol Nutr Metab. Oct. 2007;32(5):954-66.

Chano et al., "RB1CC1 insufficiency causes neuronal atrophy through mTOR signalingalteration and involved in the pathology of Alzheimer's diseases," Brain Res. Sep. 7, 2007;1168:97-105.

Chen et al., "Amyloid-beta interrupts the PI3K-Akt-mTOR signaling pathway that could beinvolved in brain-derived neurotrophic

(56) References Cited

OTHER PUBLICATIONS factor-induced Arc expression in rat cortical neurons," JNeurosci Res. Aug. 1, 2009;87(10):2297-307.
Chen et al., "HIF-1 modulates dietary restriction-mediated lifespan extension via IRE-1 inCaenorhabditis elegans," PLoS Genet. May 2009;5(5):e1000486.
Choo et al., "Rapamycin differentially inhibits S6Ks and 4E-BP1 to mediate cell-type-specificrepression of mRNA translation," Proc. Natl. Acad. Sci. USA, 105(45):17414-9, 2008.
d'Abramo et al., "Troglitazone, a peroxisome proliferator-activated receptor-gamma agonist,decreases tau phosphorylation in CHOtau4R cells," J Neurochem. Aug. 2006;98(4):1068-77.
Dakpa and Dodson-Lavelle, "A traditional Tibetan medical response to advancements in basiclongevity research," Ann N Y Acad Sci. Aug. 2009;1172:70-3.
Damjanac et al., "Dissociation of Akt/PKB and ribosomal S6 kinase signaling markers in atransgenic mouse model of Alzheimer's disease," Neurobiol Dis. Feb. 2008;29(2):354-67.
Damjanac et al., "PKR, a cognitive decline biomarker, can regulate translation via twoconsecutive molecular targets p53 and Redd1 in lymphocytes of AD patients," J Cell Mol Med.Aug. 2009;13(8B):1823-32.
Das et al., "Delivery of rapamycin-loaded nanoparticle down regulates ICAM-1 expression andmaintains an immunosuppressive profile in human CD34+ progenitor-derived dendritic cells," JBiomed Mater Res A. Jun. 15, 2008;85 (4):983-92.
Dhahbi et al., "Temporal linkage between the phenotypic and genomic responses to caloricrestriction," Proc. Natl Acad. Sci. USA, 101:5524-5529, 2004.
Edwards et al., "Annual report to the nation on the status of cancer, 1973-1999, featuring implications of age and aging on U.S. cancer burden," Cancer, 94:2766-2792, 2002.
Estep et al., "Short-term calorie restriction in male mice feminizes gene expression and alterskey regulators of conserved aging regulatory pathways," PLoS One. 2009;4(4):e5242.
Fajadet et al., "Randomized, double-blind, multicenter study of the Endeavor zotarolimus-eluting phosphorylcholine-encapsulated stent for treatment of native coronary artery lesions. Clinical and angiographic results of the Endeavor II Trial," Minerva Cardioangiol. Feb. 2007;55(1):1-18.
Fajadet et al., "Randomized, double-blind, multicenter study of the Endeavor zotarolimuselutingphosphorylcholine-encapsulated stent for treatment of native coronary artery lesions:clinical and angiographic results of the Endeavor II trial," Circulation. Aug. 22, 2006;114(8):798-806.
Galvan et al., "Long-term prevention of Alzheimer's disease-like behavioral deficits in PDAPP mice carrying a mutation in Asp664," Behav. Brain Res., 191:246-255, 2008.
Galvan et al., "Reversal of Alzheimer's-like pathology and behavior in human APP transgenicmice by mutation of Asp664," Proc. Natl. Acad. Sci. USA, 103:7130-7135, 2006.
Gillette-Guyonnet and Vellas, "Caloric restriction and brain function," Curr Opin Clin NutrMetab Care. Nov. 2008;11 (6):686-92.
Gingras et al., "Hierarchical phosphorylation of the translation inhibitor 4E-BP1," Genes Dev.,15:2852-2864, 2001.
Graziani, "Recent advances in the chemistry, biosynthesis and pharmacology of rapamycin analogs," Nat. Prod. Rep., 26(5):602-609, 2009.
Gregory et al., "Isolation and characterization of pre-rapamycin, the first macrocyclicintermediate in the biosynthesis of the immunosuppressant rapamycin by S. hygroscopicus,"Angew Chem. Int. Ed. Engl., 43(19):2551-2553, 2004.
Gregory et al., "Rapamycin biosynthesis: Elucidation of gene product function," Org. Biomol.Chem., 4 (19):3565-3568, 2006.
Guertin and Sabatini, "Defining the role of mTOR in cancer," Cancer Cell, 12:9-22, 2007.
Guertin and Sabatini, "The pharmacology of mTOR inhibition," Sci. Signal., 2(67):pe24, 2009.
Gullans, "Connecting the dots using gene-expression profiles," N Engl J Med. Nov. 9, 2006;355(19):2042-4.
Haddadi et al., "Delivery of rapamycin by PLGA nanoparticles enhances its suppressiveactivity on dendritic cells," J Biomed Mater Res A. Mar. 15, 2008;84(4):885-98.
Halagappa et al., "Intermittent fasting and caloric restriction ameliorate age-related behavioral deficits in the triple-transgenic mouse model of Alzheimer's disease," Neurobiol Dis. Apr. 2007;26(1):212-20.
Hansen et al., "A role for autophagy in the extension of lifespan by dietary restriction in C.elegans," PLoS Genetics, 4 (2):e24, 2008.
Hansen et al., "Lifespan extension by conditions that inhibit translation in Caenorhabditis elegans," Aging Cell, 6:95-110, 2007.
Harrison et al., "Rapamycin fed late in life extends lifespan in genetically heterogeneous mice," Letters, 460:392-395, 2009.
Honjoh et al., "Signalling through RHEB-1 mediates intermittent fasting-induced longevity inC. elegans," Nature. Feb. 5, 2009;457(7230):726-30.
Ai-Ling, L et al, "Chronic Rapamycin Restores Brain Vascular Integrity and Function Through NO Synthase Activation and Improves memory in Symptomatic Mice Modeling Alzheimer's Disease", Journal of Cerebral Blood Flow & Metabolism, vol. 33, 1412-1421, Sep. 2013.
Bell, R and Zlokovic, B, "Neurovascular mechanisms and Blood-Brain Barrier Disorder in Alzheimer's Disease", Acta Neuropathology, Jul. 2009, 118(1): 103-113.
Caccamo, A et al, "Molecular Interplay Between Mammalian Target of Rapamycin (mTOR), Amyloid-$\beta$, and Tau", Journal of Biological Chemistry, Apr. 23, 2010, vol. 285, No. 17, p. 13107-13121.
Halloran, J et al, "Chronic Inhibition of mTOR by Rapamycin Modulates Cognitive and Non-Cognitive Components of Behavior Throughout Lifespan in Mice", Neuroscience, Jun. 2012, vol. 223: p. 102-113, US.
Jhunjhunwala, J et al, Delivery of Rapamycin to Dendritic Cells Using Degradable Microparticles, US National Library of medicine, National Institutes of Health, Feb. 10, 2009; 133(3) 191-197 doi:10. 1016/j.conrel,2008.10.011.
Majumder, S et al, "Inducing Autophagy by Rapamycin Before, but Not After, the Formation of Plaques and Tangles Ameliorates Cognitive Deficits", PLos One, Sep. 2011, vol. 6, Issue 9, Emory University, US.
Parlar, A et al, "Posttransplantation Therapeutic Rapamycin Concentration Protects Nitric Oxide-Related Vascular Endothelial Function: Comparative Effects in Rat Thoracic Aorta and Coronary Endothelial Cell Culture", Jun. 2010, Transplantation Proceedings, Elsevier Inc., Orlando, FL, vol. 42(5), p. 1923-1930.
Ravikumar, B et al, "Rapamycin Pre-Treatment Protects Against Apoptosis", Human Molecular Genetics, vol. 15, No. 7,p. 1209-1216, Apr. 2006, Oxford University Press, Surrey, United Kingdom.
Spilman, P et al, "Inhibition of MTOR by Rapamycin Abolishes Cognitive Deficits and Reduces Amyloid-$\beta$ Levels in a Mouse Model of Alzheimer's Disease", Apr. 2010, vol. 5, Issue 4, PLoS One vol. 5(4): p. e9979.
Zlokovic, B, "Neurovascular Pathways to Neurodegeneration in Alzheimer's Disease and Other Disorders", National Rev Neuroscience, vol. 12(12): p. 723-738.

\* cited by examiner

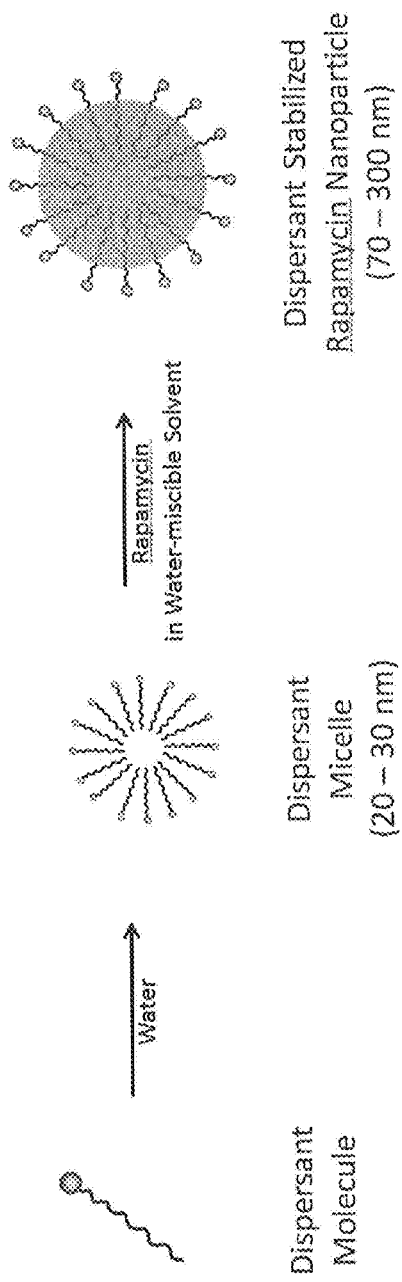

ORAL RAPAMYCIN NANOPARTICLE PREPARATIONS

CLAIM OF PRIORITY TO PRIOR APPLICATIONS

This application claims the benefit of U.S. Provisional Application Ser. No. 61/922,800, filed on Dec. 31, 2013, and U.S. Provisional Application Ser. No. 61/803,525, filed on Mar. 20, 2013, both entitled "Oral Rapamycin Nanoparticle Preparations", the entire disclosures of which are hereby incorporated into the present disclosure.

NONPUBLICATION REQUESTED—NONPROVISIONAL APPLICATION

This application is a nonprovisional application under 37 CFR 1.53(b) and is submitted with an accompanying nonpublication request in accordance with 35 CFR U.S.C. §122(b). Accordingly, the subject matter of this application is to be maintained in secrecy until and unless Applicant allows a patent to issue based on this application.

STATEMENT REGARDING FEDERALLY SPONSORED RESEARCH

Not applicable

BACKGROUND OF INVENTION

1. Field of the Invention

The present invention relates generally to manufacture and use of mTOR inhibitors for oral administration in the prevention and treatment of medical maladies in humans and other animals. More particularly, the invention relates to manufacture and use of preparations for oral administration that include an mTOR inhibitor together with polymers and stabilizers for prevention and treatment of medical maladies, most especially in the fields of oncology, neurology, and healthy lifespan extension in humans and other animals.

2. Description of Related Art

Rapamycin (also known as sirolimus) is a well-known pharmaceutical agent that has long been used to minimize organ transplant rejection. Rapamycin and its analogs and derivatives famously act to inhibit its namesake metabolic pathway—the mammalian target of rapamycin ("mTOR"). The critical metabolic roles of the mTOR pathway have long led to broad speculation about possible medical uses for rapamycin outside of organ transplant rejection. However, despite the success with prevention of transplant rejection, and despite the many long-felt needs and corresponding tremendous efforts in developing rapamycins for other indications, effective use of rapamycin for treating or preventing other disorders has not been widely successful and has been very limited at best. The likely reasons why it has not been widely used outside of preventing organ transplant rejection are varied and speculative, ranging from its raw chemistry to poor compliance and scary side effects (rumored to include high mortality rates largely due to dosing in early trials from the 1960s or 1970s).

For additional technical descriptions and a detailed description of the related art, this application incorporates by reference the entirety of US Patent Application 2012/0064143 A1, Inhibition of Mammalian Target of Rapamycin, which has original priority dating to Nov. 11, 2008.

Particular formulations taught in US Patent Application 2012/0064143 (the "2008 Discoveries") provided particles or "cores" containing the active rapamycin ingredient, and those cores were microencapsulated within a polymer matrix, for oral administration of the rapamycin. The rapamycin cores were microencapsulated using a spinning disk atomization coating process with a polymer matrix known under the "Eudragit S-100" name. The Eudragit S-100 polymer matrix includes a particular methacrylate polymer that is generally stable at pH levels below 7 and was used to protect the rapamycin from degrading in the acidic conditions of the stomach. Then, once the microencapsulated rapamycin entered basic conditions (i.e., pH greater than 7) within the intestines, the matrix would dissolve and, theoretically, the undegraded rapamycin would be absorbed through the intestinal walls and become bioavailable for its intended medical purposes.

Unfortunately, theory and practice do not always match perfectly. Despite tremendous hope for broad efficacy of the orally administered use of such microencapsulated rapamycin preparations, and despite widespread national and international attention to the 2008 Discoveries, significant concerns remained about whether sufficiently predictable and effective levels of rapamycin could be reliably delivered to the body in this form. For reasons that long remained uncertain in practice, stability of the basic rapamycin molecule within such formulations has been less reliable than desired, and uncertainties have mounted with respect to whether enteric absorption levels can be reliable enough for adequate market acceptance of the 2008 Discoveries. Consequently, there is a need for improved encapsulated rapamycin preparations—preparations that still capitalize on the 2008 discoveries but that improve various performance characteristics, such as storage stability, biodistribution, dosage cost, etc.

In addition, because the potential applications are so wide and varied and yet relatively unproven for an oral form of rapamycin, that wide variety itself presents an impediment to realizing publically available use of such a preparation. Given the market dynamics and regulatory requirements of pharmaceutical industries, a successful effort to actually make embodiments of the 2008 Discoveries available for use by the public would require much more than minimizing uncertainties about the preparation itself. A successful effort to do so must identify and validate a particular, highly-impactful indication for which the benefits of using a microencapsulated rapamycin would be relatively irrefutable, and the effort must likewise develop corresponding methods and strategies for effectively and reliably addressing as much.

SUMMARY OF THE INVENTION

While the present invention is multifaceted, it can be embodied in numerous improved forms of encapsulated rapamycins and in methods for reliably producing and predictably dosing and administering these improved forms. The improved forms of encapsulated rapamycin preferably provide rapamycin nanoparticles within a protective polymer matrix for oral administration of rapamycin. The result is not only more stable (i.e., less susceptible to degradation caused by moisture, pH and oxidation), but is also more bioavailable and efficacious, with surprisingly better biodistribution, for treatment and prevention of genetically-predisposed disorders and age-related disorders, especially in the fields of oncology and neurology in humans and other animals, with some prospects in surprising segments of the autoimmunology field.

The various embodiments improve on the related art, including by optimizing stability, manufacturability, bioabsorption, biodistribution, dosage cost, efficacy and the like. Although the embodiments addressed below do not compose an exhaustive list, this specification describes embodiments comprising controlled release encapsulated rapamycin; rapamycin nanoparticle inclusions; rapamycin nanoparticle morphology; free radical scavengers and oxidative stabilizers; and an albumin-rapamycin nanoparticle. Some particular embodiments have been especially surprising, particularly embodiments that use mTOR-inhibiting nanoparticles formed within molecular aggregations controllably created from sodium cholate (or equivalent), to provide reliable production methods and markedly better bioavailability and biodistribution.

Many other objects, features and advantages of the present invention will become apparent to those of ordinary skill in the art, particularly after a thorough review of the public literature in the field, and all the more from the following detailed descriptions and accompanying illustrations and claims. It should be understood, however, that the detailed description and the specific examples, while indicating preferred embodiments of the invention, are given by way of illustration only, since various changes and modifications within the spirit and scope of the invention will become apparent to those skilled in the art from these detailed descriptions.

BRIEF DESCRIPTION OF THE DRAWINGS

FIG. 1a is a schematic illustrating the microscopic general process of creating rapamycin nanoparticles in keeping with some described embodiments of the present invention.

FIG. 1b sets forth a formula for estimating the approximate number of rapamycin molecules in a nanoparticle in keeping with some described embodiments of the present invention.

FIG. 2b is a picture depiction of a nanoparticle dispersion typical of Step 2 of FIG. 2a.

DETAILED DESCRIPTION OF PREFERRED EMBODIMENTS

Figure 2A:
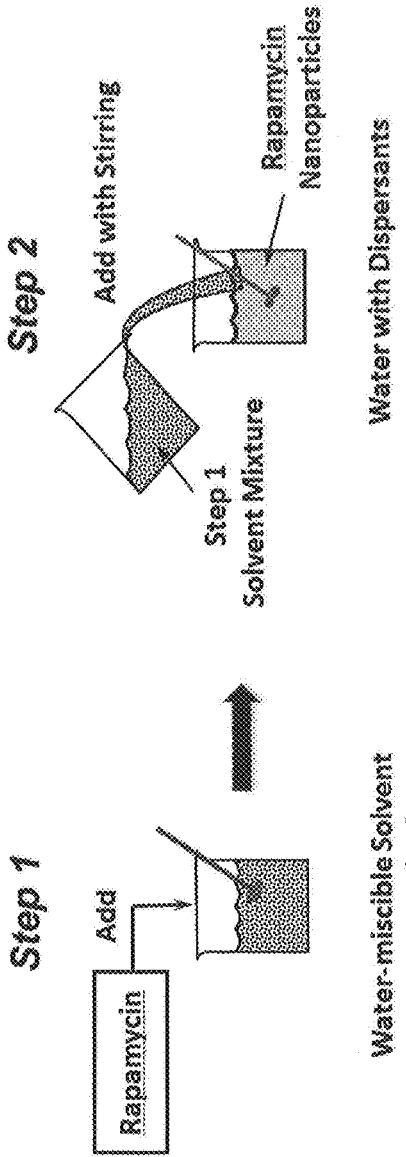
FIG. 2a provides a schematic illustrating the macroscopic general process of creating rapamycin nanoparticles in keeping with some described embodiments of the present invention.
Figure 2C:
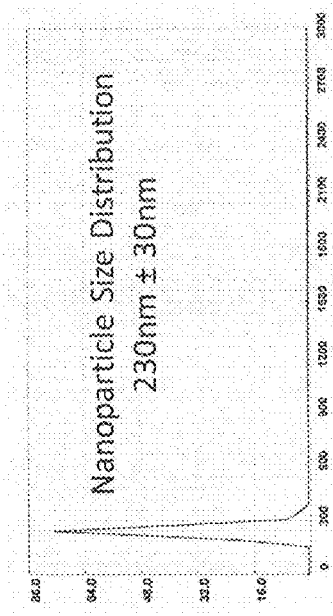
FIG. 2c sets forth a nanoparticle size distribution range for nanoparticles made in keeping with some described embodiments of the present invention.
Figure 2B:
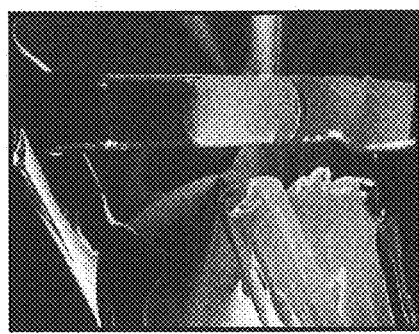
Figure 3:
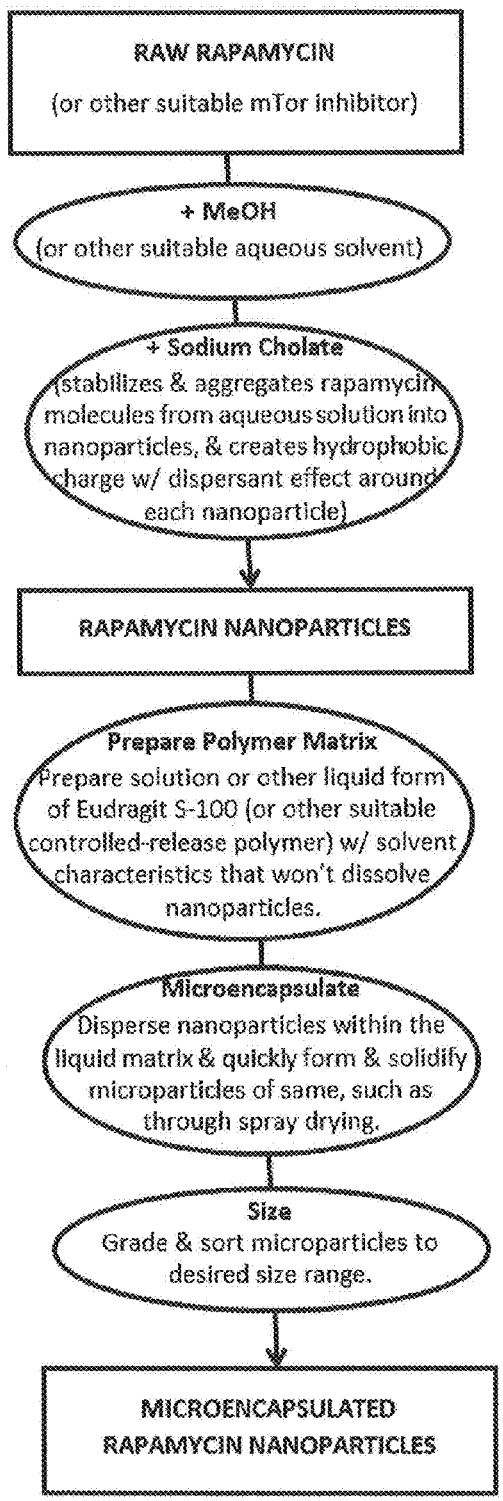
FIG. 3 is a flow chart illustrating the process taking raw rapamycin and producing microencapsulated rapamycin nanoparticles in keeping with some described embodiments of the present invention.
Figure 4:
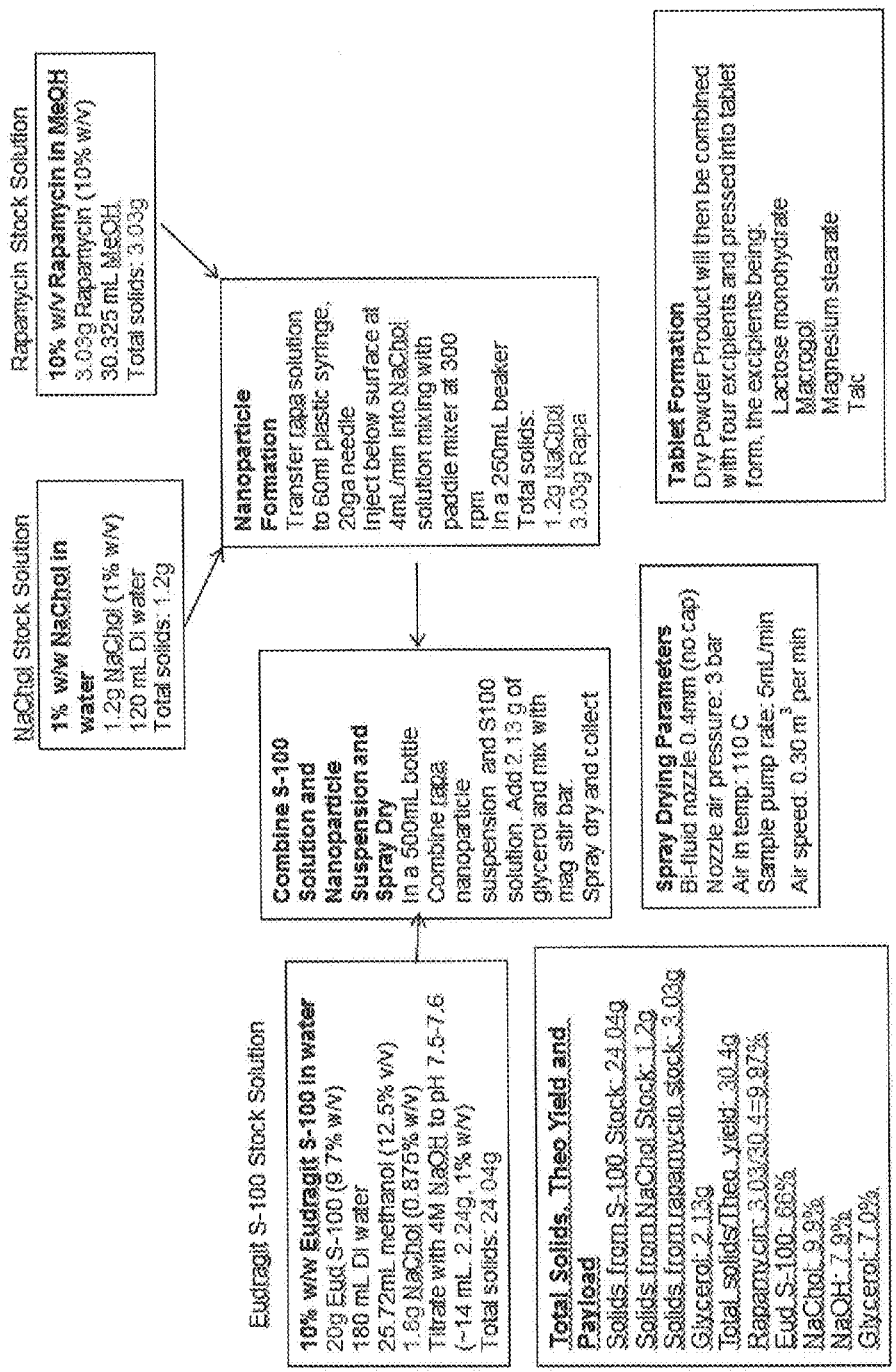
FIG. 4 is a flow chart depicting a process of producing microencapsulated rapamycin nanoparticles in Eudragit S-100, as implemented by some embodiments of the present invention.

The following examples are included to demonstrate preferred embodiments of the invention. It should be appreciated by those of skill in the art that the techniques disclosed in these examples are thought to represent techniques that function well in the practice of the invention, and thus can be considered to constitute preferred modes for its practice. However, in light of the present disclosure, those of skill in the art should appreciate that many changes can be made in the specific embodiments which are disclosed while still obtaining a like or similar result without departing from the spirit and scope of the invention.

For purposes of these descriptions, a few wording simplifications should also be understood as universal, except to the extent otherwise clarified in a particular context either in the specification or in any claims. The use of the term "or" in the specification is used to mean "and/or" unless explicitly indicated to refer to alternatives only, or unless the alternatives are inherently mutually exclusive. When referencing values, the term "about" is used to indicate an approximate value, generally one that includes the standard deviation of error for any particular embodiments that are disclosed or that are commonly used for determining such value. "A" or "an" may mean one or more, unless clearly indicated otherwise. Such "one or more" meanings are most especially intended when references are made in conjunction with open-ended words such as "having," "comprising" or "including." Likewise, "another" may mean at least a second or more.

General mTor-Inhibiting Nanoparticle Embodiments

Preferred embodiments of the present invention provide an improved form of encapsulated rapamycin—an encapsulated rapamycin nanoparticle that is more stable and bioavailable, which enhances efficacy and predictability and ensures better biodistribution while also allowing improved patient compliance relative to raw rapamycin, as well as being produced at a reasonable cost. The improved form of encapsulated rapamycin preferably provides the rapamycin nanoparticles within a polymer matrix, forming an encapsulated rapamycin nanoparticle in a single drug delivery structure for oral administration of rapamycin. The polymer matrix, more particularly, is a controlled release matrix, as descried elsewhere in these descriptions. This encapsulated rapamycin nanoparticle may also be referred to as an enteric-coated rapamycin nanoparticle. In addition, many of the preferred embodiments also include a stabilizing compound (for our purposes, a "stabilizer") within the controlled release matrix either to improve compatibility of the rapamycin with the controlled release matrix, to stabilize the crystalline morphology of the rapamycin, or to help further prevent degradation of the rapamycin, particularly when the encapsulated rapamycin nanoparticle is exposed to air, atmospheric moisture, or room temperature or warmer conditions. Particularly preferred embodiments incorporate the stabilizers within each rapamycin nanoparticle, although certain aspects of the invention may be embodied with stabilizers on the surface of the encapsulated rapamycin nanoparticles or otherwise dispersed in the controlled release matrix. To different levels depending on the particular approach used for producing the nanoparticles, with or without other additives, the result is more efficacious for treatment and prevention of genetically-predisposed disorders and age-related disorders, especially in the fields of oncology and neurology in humans and other animals.

Rapid anti-solvent precipitation, or controlled precipitation, is a preferred method of preparing the rapamycin nanoparticles, which provides for minimal manipulation of the rapamycin and exquisite control over nanoparticle size and distribution, and crystallinity of the rapamycin. Several controlled precipitation methods are known in the art, including rapid solvent exchange and rapid expansion of supercritical solutions, both of which can be implemented in batch or continuous modes, are scalable, and suitable for handling pharmaceutical compounds. Preferred embodiments use an anionic approach, producing micelles or other molecular aggregations of amphopathic compounds (e.g., sodium cholate or similar surfactants with amphopathic tendencies) in concentrations greater than their critical micelle concentration. Through the controlled precipitation, the rapamycin is mixed and dissolved into an aqueous miscible solvent that contains stabilizing compounds (e.g., sodium cholate). The resultant fluid is injected into rapidly stirred water containing an appropriate aqueous soluble dispersant. After mixing, the effects of solubility cause the rapamycin to partition to the micelle cores. Appropriate solvents and dispersants are discussed in greater detail below. The results create a hydrophobic nanoparticle decorated with sodium cholate. The sodium cholate results in a hydrophilic surface, stabilizing the nanoparticles in the aqueous media and thereby preventing aggregation and particle growth. This product ensures enhanced and prolonged rapamycin stability—i.e., improved resistance to moisture degradation and/or oxidation for the final product.

Rapamycin nanoparticles prepared by controlled precipitation methods can be stabilized against irreversible aggregation, Ostwald ripening, and/or reduced dispersibility, by control of colloid chemistry, particle surface chemistry and particle morphology. For example, nanoparticles prepared by antisolvent solidification can be stabilized by ionic and non-ionic surfactants that adsorb to nanoparticle surfaces and promote particle colloid stability through either charge repulsion or steric hindrance, respectively. Moreover, stabilizers can affect nanoparticle crystallinity, which may be preferred to promote different biodistribution and bioavailability in certain indications.

Rapamycin nanoparticles can consist of molecular rapamycin bound by suitable methods to other nanoparticles. Suitable methods of attaching rapamycin to a nanoparticle carrier or substrate may include physical adsorption through hydrogen van der Waals forces or chemisorption through covalent or ionic bonding. Nanoparticle substrates may be either natural or synthetic, and modified to promote specific interactions with rapamycin. Natural nanoparticles include albumin and other proteins, as well as DNA. Synthetic nanoparticles include organic and inorganic particulates, micelles, liposomes, dendrimers, hyperbranched polymers, and other compounds.

The rapamycin nanoparticles can be processed by any suitable method, such as by milling, high pressure atomization, or rapid anti-solvent precipitation. Milling is suitable provided care is taken to minimize both rapamycin degradation and particle agglomeration. Rapamycin degradation can be reduced with the aid of cooling or cryogenic processes. Agglomeration due to the increased surface area and concomitant adhesive forces can be reduced by the use of dispersants during the milling process.

Individual rapamycin nanoparticles are preferably sized in the range between about 1 nanometer and about 1 micron. Smaller sized rapamycin nanoparticles are preferred, preferably at less than 1 micron in diameter, for various reasons, including better control of final particle size, improved stability within the nanoparticles, and the ability to tune bioavailability by controlling the crystallinity and composition of the rapamycin nanoparticles.

Manufacturing approaches for some embodiments of the encapsulated rapamycin nanoparticle drug delivery structure include creating a solution of the controlled release matrix, with the rapamycin nanoparticles dispersed therein, in appropriate proportion and producing a heterogeneous mixture. The solvent for such mixtures can be a suitable volatile solvent for the controlled release matrix, although it is preferred the solvent be either a poor solvent or non-solvent for the rapamycin nanoparticles so that when the rapamycin nanoparticles are dispersed into the controlled release matrix solution they remain as discrete nanoparticles. The resulting dispersion of rapamycin nanoparticles in the controlled release matrix solution can then be reduced to a dry particulate powder by a suitable process, thereby resulting in microparticles of a heterogeneous nature comprised of rapamycin nanoparticles randomly distributed in the controlled release matrix. The particulate powder may also be tailored by a suitable process to achieve a preferred particle size for subsequent preparation, which may be from about 20 to about 70 microns in diameter.

The rapamycin nanoparticles are microencapsulated with the controlled release matrix using a suitable particle-forming process to form the encapsulated rapamycin nanoparticle. An example of a particle-forming process is spinning disk atomization and drying. For a detailed discussion of the apparatus and method concerning the aforementioned spin disk coating process, this application incorporates by references US Patent Applications 2011/221337 and 2011/220430, respectively. Alternatively, for example, the encapsulated rapamycin nanoparticles can be prepared by spray drying.

In some embodiments, not all of the rapamycin nanoparticles will be encapsulated within the controlled release matrix. Instead the rapamycin nanoparticles may be enmeshed with the controlled release matrix, with some of the rapamycin nanoparticles wholly contained within the controlled release matrix while another other rapamycin nanoparticles apparent on the surface of the drug delivery structure, constructed in appearance similar to a chocolate chip cookie.

Depending on the size of the rapamycin nanoparticles, the encapsulated rapamycin (i.e., the microparticles that include multiple nanoparticles distributed within the enteric matrix) are preferably of diameter between 10 and 50 microns, although diameters as large as 75 microns may be suitable for alternatives with corresponding compromises due to the larger size.

The controlled release matrix of the encapsulated rapamycin nanoparticles can be selected to provide preferred release characteristics of the encapsulated rapamycin nanoparticles. For example, the matrix may be pH sensitive to provide generally enteric release of the rapamycin and/or controlled release in predictable segments of the intestines. Enteric release of the rapamycin is preferred to achieve improved absorption and bioavailability of the rapamycin. Many materials suitable for enteric release are known in the art, including fatty acids, waxes, natural and synthetic polymers, shellac, and other materials. Polymers are a preferred enteric coating and may include copolymers of methacrylic acid and methyl methacrylate, copolymers of methyl acrylate and methacrylic acid, sodium alginate, polyvinyl acetate phthalate, and various succinate or phthalate derivatives of cellulose and hydroxpropyl methyl cellulose. Synthetic polymers, such as copolymers of methacrylic acid and either methyl acrylate or methyl methacrylate, are preferred enteric release polymers due the ability to tune the dissolution pH range of these synthetic polymers by adjusting their comonomer compositions. Examples of such pH sensitive polymers are EUDRAGIT® polymers (Evonik Industries, Essen, Germany). Specifically, EUDRAGIT® S-100, a methyl methacrylate and methacrylic acid copolymer with comonomer ratio of 2:1, respectively, has a dissolution pH of about 7.0, thereby making is suitable for enteric release of rapamycin.

The encapsulated rapamycin nanoparticles may be delivered in various physical entities including a pill, tablet, or capsule. The encapsulated rapamycin nanoparticles may be pressed or formed into a pellet-like shape and further encapsulated with a coating, for instance, an enteric coating. In another embodiment, the encapsulated rapamycin nanoparticles may be loaded into a capsule, also further enterically coated.

Various performance enhancing additives can be added to the encapsulated rapamycin nanoparticles. For example, additives that function as free radical scavengers or stabilizers can be added to improve oxidative and storage stability of the encapsulated rapamycin nanoparticles. Free radical scavengers are preferably chosen from the group that consists of glycerol, propylene glycol, and other lower alcohols. Additives alternatively incorporate antioxidants, such as α-tocopherol (vitamin E), citric acid, EDTA, α-lipoic acid, or the like.

Methacrylic acid copolymers with methyl acrylate or methyl methacrylate are moderate oxygen barriers. Furthermore, these polymers will exhibit an equilibrium moisture content. Oxygen transport due to residual solvent, moisture or other causes, can lead to degradation of the encapsulated rapamycin nanoparticles. Oxygen barrier materials can be added to the encapsulated rapamycin nanoparticles formulation to improve oxygen barrier properties. Preferred oxygen barrier polymers compatible with the preferred polymers are polyvinyl alcohol (PVA) and gelatin.

Preferred Microparticle and Nanoparticle Embodiments

Preferred embodiments with rapamycin nanoparticle inclusions comprise discrete nanoparticles of rapamycin heterogeneously dispersed in a controlled release matrix. As illustrated in accompanying drawings, the rapamycin nanoparticles are prepared by a suitable method and may contain additives to promote nanoparticle stability, modify rapamycin crystallinity, or promote compatibility of the rapamycin nanoparticles with the controlled release matrix. The controlled release matrix is formulated to promote release of rapamycin to specific parts of the body, such as the intestine, to enhance oxidative and storage stability of the encapsulated rapamycin nanoparticles, and to maintain the discrete, heterogeneously distributed nature of the rapamycin nanoparticles.

Rapamycin nanoparticles are preferably prepared by antisolvent precipitation or solidification, also sometimes referred to as controlled precipitation or solidification. Antisolvent solidification is a preferred approach as it provides exquisite control of particle size and distribution, particle morphology, and rapamycin crystallinity. For example, it is possible to prepare nanoparticles with narrow particle size distribution that are amorphous, crystalline, or combinations thereof. Such properties may exhibit additional benefits, by further controlling the biodistribution and bioavailability of rapamycin in specific indications.

Rapamycin is dissolved in a suitable water-miscible solvent and then rapidly injected into rapidly stirred water containing an appropriate aqueous soluble dispersant. Water-miscible solvents for rapamycin include methanol, ethanol, isopropyl alcohol, acetone, dimethylsulfoxide, dimethylacetamide, n-methylpyrolidone, tetrahydrofuran, and other solvents. Low boiling point, high vapor pressure water-miscible solvents are preferred to facilitate their removal during subsequent microparticle formation. Some preferred water-miscible solvents are methanol, acetone, and isopropyl alcohol. A preferred water-miscible solvent is methanol. Some aqueous soluble dispersants include ionic surfactants such as sodium dodecyl sulfate and sodium cholate, non-ionic surfactants such as Pluronics, Poloxomers, Tweens, and polymers, such as polyvinyl alcohol and polyvinylpyrolidone. Some preferred aqueous-soluble dispersants are sodium cholate, Pluronic F-68, and Pluronic F-127. A preferred aqueous-soluble dispersant is sodium cholate, which provides surprisingly beneficial properties in the present application.

Not only is sodium cholate a surfactant and a dispersant, in the preferred embodiments, it serves to produce multimolecular structures which tend to cause aggregation of rapamycin within those structures, particularly when the pH and other conditions of the aqueous solution are controlled to allow aggregation of the rapamycin from that aqueous solution. The resulting process allows for rapamycin nanoparticle production that not only tends to produce nanoparticles in highly predictable size ranges, but also provides a resulting nanoparticle with surprisingly desirable levels of colloidal stability. Moreover, while sodium cholate tends to be a polar molecule as well as an amphoteric surfactant, it induces an ionic charge in each hydrophilic nanoparticle when enmeshed in the Eudragit matrix. It is believed that when the nanoparticle is released from the Eudragit matrix within the animal subject's enteric passages where conditions are basic, the same properties may cause the nanoparticle to be more readily received and absorbed through the intestinal walls.

Rapamycin is dissolved in the water-miscible solvent at a concentration of about 0.01% w/v to about 10.0% w/v preferably about 0.1% w/v to about 1.0% w/v. The aqueous-soluble dispersant is dissolved in water at a concentration above its critical micelle concentration, or CMC, typically at about 1 to about 10 times the CMC. The rapamycin solution is injected into the aqueous-soluble dispersant solution with agitation at a volumetric ratio of about 1:10 to about 1:1, preferably about 1:5 to about 1:1.

The controlled release matrix is prepared from a water-soluble polymer, preferably a copolymer of methacrylic acid with either methyl acrylate or methyl methacrylate, such as those marketed under the trade name of EUDRAGIT® and having pH-dependent dissolution properties. More preferably the controlled release matrix is comprised of EUDRAGIT® S-100, although other water-soluble enteric controlled release would be suitable. Water-soluble controlled release matrices are selected so as either not to compromise the integrity of rapamycin nanoparticles or to provide a medium in which rapamycin nanoparticles may be prepared by the controlled precipitation methodology described previously.

In preparing the water-soluble polymer, it is preferable to maintain conditions that do not compromise the integrity of the rapamycin nanoparticles. Firstly, since the rapamycin nanoparticles are susceptible solubilization by certain co-solvents, it is important to maintain a suitable quantity of certain co-solvents to achieve controlled release matrix solubility while not deleteriously affecting the morphology of the rapamycin nanoparticles. Secondly, rapamycin nanoparticles will be susceptible to chemical degradation by high pH; therefore, it is important to modulate the controlled release matrix solution pH so that rapamycin is not chemically altered. It is preferable the controlled release matrix solution pH be maintained below about pH 8. Lastly, it is preferable to achieve near to complete solubilization of the controlled release matrix in solution so that microencapsulation of the rapamycin nanoparticles by the controlled release matrix in subsequent processing steps may proceed with high efficiency. When using the EUDRAGIT® S-100 as the controlled release matrix, it is preferable to achieve a controlled release matrix solution by using a combination of co-solvents and solution pH modulation. It is preferable the co-solvents be about 40% or less by volume. Similarly, it is preferable that the pH of the controlled release matrix solution be about 8 or less, such that the EUDRAGIT® S-100 is not completely neutralized and is preferably only about 80% or less neutralized. These preferred conditions achieve nearly complete to complete solubilization of the EUDRAGIT® S-100 in a medium that is mostly aqueous and that maintains the integrity of the rapamycin nanoparticles, therefore leading to their microencapsulation by the controlled-release matrix in subsequent processing steps.

The rapamycin nanoparticles prepared by the preferred controlled precipitation method are added to the aqueous solution of the controlled released matrix, resulting in a nanoparticle dispersion in the solubilized controlled release matrix. Alternatively, the rapamycin solubilized in a suitable or preferred co-solvent can be dispersed into the aqueous solution of controlled release matrix leading to controlled precipitation of rapamycin particles, thereby leading to a rapamycin nanoparticle dispersion in fewer processing steps, but of appropriate composition to permit subsequent microencapsulation processing.

As an alternative embodiment, the encapsulated rapamycin nanoparticles are created using pre-existing nanoparticle substrates, such as albumin, to create, in the case of albumin, "albumin-rapamycin nanoparticles." Within this general class of alternatives, preferred approaches for creating the albumin-rapamycin nanoparticles involve encapsulating rapamycin within albumin nanoparticles or preferentially associating rapamycin with albumin nanoparticles through physical or chemical adsorption. The albumin nanoparticles themselves are preferably formed from human serum albumin, a plasma protein derived from human serum.

More particularly, this embodiment preferably involves use of a therapeutic peptide or protein that is covalently or physically bound to albumin, to enhance its stability and half-life. With the albumin stabilized, the rapamycin is mixed with the stabilized albumin in an aqueous solvent and passed under high pressure to form rapamycin-albumin nanoparticles in the size range of 100-200 nm (comparable to the size of small liposomes).

Preferred embodiments also address degradation risks and other limits imposed by the related art by preparing encapsulated rapamycin nanoparticles as a heterogeneous mixture of rapamycin nanoparticles in a polymer matrix. Distributed nanoparticles are morphologically different than homogeneous rapamycin; and are less susceptible to degradation because of the bulk nature of the nanoparticles compared to the smaller size of molecular rapamycin.

Examples of Preferred mTor Inhibiting Preparations

Example 1—Development of Methods to Produce Rapamycin Nanoparticles

Rapid solvent exchange was used to examine the formation of rapamycin nanoparticles. Three water-miscible solvents and three water-soluble surfactants were selected to study their respective effects on the formation and morphology of rapamycin nanoparticles. The water-miscible solvents were isopropyl alcohol (Solvent 1), acetone (Solvent 2), and methanol (Solvent 3). The water-soluble surfactants were Pluronic F-68 (Dispersant 1, a non-ionic PEO-PPO-PEO block copolymer), Pluronic F-127 (Dispersant 2, a non-ionic PEO-PPO-PEO block copolymer), and sodium cholate (Dispersant 3, an anionic surfactant). Rapamycin was dissolved in each of the water-miscible solvents at a concentration of 0.25% w/v. The water-soluble surfactants were dissolved in deionized water at concentrations of 0.5% w/v, 0.5% w/v, and 1.0% w/v, respectively, for each of the dispersants. Each experimental combination (e.g. NP-1 to NP-9 in following table) consisted of 5 mL of rapamycin solution and 25 mL of surfactant solution, resulting in a dilution factor of 1:5 solvent:water. 25 mL of surfactant solution was transferred to a 50 mL beaker and stirred with the aid of magnetic mircostirbar. Rapamycin solution was rapidly injected at 500 uL increments with the aid of a micropipette with the pipette tip placed below the surface of the rapidly stirred surfactant solution. The visual appearance of the resulting nanoparticles and their colloidal stability after 24-hours were qualitatively assessed. The following table summarizes the qualities of the rapamycin nanoparticle dispersions. Qualitatively, rapamycin nanoparticle dispersions having a colorless to blue, opalescent appearance will have particle sizes on the order of less than about 300 nm as evidenced by their interaction with the ultraviolet wavelengths of visible light. Whereas, dispersions having a more white appearance will have particle sizes larger than about 300 nm due to their interaction with the broader spectrum of visible light. Rapamycin nanoparticle formulations NP-7 and NP-9 were selected as preferred methods of nanoparticle preparation.

|  | Dispersant 1 | Dispersant 2 | Dispersant 3 |
| --- | --- | --- | --- |
| Solvent 1 | NP-1: White, settled, resdispersible | NP-2: Blue, opalescent, settled, redispersible | NP-3: Clear, aggregated, redispersible |
| Solvent 2 | NP-4: Blue, opalescent, some settling | NP-5: White, settled, redispersible | NP-6: Blue, opalescent, settled, redispersible |
| Solvent 3 | NP-7: Blue, opalescent, stable | NP-8: Blue to white, settled, redispersible | NP-9: Blue, opalescent, stable |

Example 2—Preparation of a High Concentration Rapamycin Nanoparticle Dispersion

The water-miscible solvent and water-soluble dispersant of NP-9 from Example 1 was used to prepare rapamycin nanoparticles. 656 mg of rapamycin were dissolved in 6.56 mL of Solvent 3 to yield a 1.0% w/v solution. This volume of rapamycin solution was injected into 26.25 mL of 1.0% w/v Dispersant 1 in deionized water. The resulting rapamycin nanoparticle dispersion had a final rapamycin content of 2.4% w/w. The particle size of the dispersion was determined by dynamic light scattering to be 230 nm±30 nm with a single peak.

Example 3—Preparation of a Water-Soluble Enteric Coating 3.5 g of EUDRAGIT® S-100 were added to 70 mL of deionized water with light stirring, resulting in a white dispersion. 1.4 g of sodium hydroxide were added to the dispersion with continued stirring. The resulting dispersion gradually turned clear and colorless indicating an aqueous solution of S-100. The estimated concentration of sodium hydroxide was 0.5N.

Example 4—Preparation of a Feedstock Containing Rapamycin Nanoparticles and a Water-Soluble Enteric Coating Rapamycin nanoparticles were prepared as described in Example 2 and then slowly added to an aqueous solution of EUDRAGIT® S-100 prepared as in Example 3. The ratio of rapamycin to S-100 was 1:9, or 10% wt. rapamycin payload. The resulting dispersion was allowed to stir for several minutes to observe stability. After one hour, the dispersion had transformed to a clear yellow, indicating destruction of the rapamycin nanoparticles and a change in the rapamycin. Addition of a small amount of acetic acid to reduce the solution pH to below neutral resulted in a clear, colorless solution.

Example 5—Preparation of Water-Soluble Enteric Coating with a Water-Miscible Co-Solvent 3.5 g of EUDRAGIT® S-100 were added to 30/70 v/v methanol/deionized water, resulting in a white dispersion. The dispersion was stirred continuously until a clear solution was formed.

Example 6—Preparation of a Feedstock Containing Rapamycin Nanoparticles and a Water-Soluble Enteric Coating Rapamycin nanoparticles were prepared as described in Example 2 and then slowly added to an aqueous solution of EUDRAGIT® S-100 prepared as in Example 5. The ratio of rapamycin to S-100 was 1:9, or 10% wt. rapamycin payload. The white dispersion was allowed to stir for several minutes after which the dispersion was transformed into a clear solution indicating the rapamycin nanoparticles had been destroyed.

Example 7—Preparation of a Partially-Neutralized, Water-Soluble Enteric Coating with a Water-Miscible Co-Solvent 3.5 g of EUDRAGIT® S-100 were added to 10/90 v/v methanol/deionized water, resulting in a white dispersion. The dispersion was titrated to clarity with 2.000 mL of 4.8M sodium hydroxide. The estimated neutralization of the S-100 was 78%.

Example 8—Preparation of a Feedstock Containing Rapamycin Nanoparticles and a Water-Soluble Enteric Coating Rapamycin nanoparticles were prepared as described in Example 2 then slowly added to an aqueous solution of EUDRAGIT® S-100 as prepared in Example 7. The ratio of rapamycin to S-100 was 1:9, or 10% wt. rapamycin payload. The resulting white dispersion remained stable for several hours as indicated by no change in color or change in optical clarity. The final pH was 7.5. The particle size of the final dispersion was determined by dynamic light scattering to be 756 nm±52 nm with a single peak and indicating possible clustering of the rapamycin nanoparticles in the resulting feedstock.

Example 9—Preparation of a Feedstock Containing Rapamycin Nanoparticles and a Water-Soluble Enteric Coating The rapamycin solution used in Example 2 was injected with stirring into the aqueous solution of EUDRAGIT® S-100 prepared in Example 7. The ratio of rapamycin to S-100 was 1:9, or 10% wt. rapamycin payload. A blue, opalescent colloid was formed and it remained stable for several hours as indicated by no change in color or change in optical clarity. The final pH was 7.5. The particle size of the final dispersion was determined by dynamic light scattering to be 305 nm±60 nm with a single peak.

Example 10—Spray Drying of Feedstock Containing Rapamycin Nanoparticles and a Water-Soluble Enteric Coating The feedstocks prepared in Examples 8 and 9 were spray dried and analyzed for rapamycin content. Particles prepared from Example 8 had a rapamycin content of 9.5% wt. (87% rapamycin yield). Particles prepared from Example 9 had a rapamycin content of 7.9% wt. (80% rapamycin yield).

Example 11—Storage Stability of Enteric-Coated Encapsulated Rapamycin Nanoparticles Microparticles prepared by spray drying in Example 10 were stored under controlled conditions at room temperature and 50% relative humidity. Samples were analyzed weekly for rapamycin content. All samples maintained at least 95% of their original rapamycin content at all times points for at least three weeks.

Uses of the Oral mTor Preparations

When orally administered daily, or at other regular frequencies, in correspondingly effective doses, pharmaceutical preparations prepared according to the foregoing descriptions, and their equivalents, are effective for preventing and treating various maladies in humans and other animals, and for reducing the progression of those maladies and their sequelae.

For example, such oral administration enables a human subject or his/her caregiver to prevent or treat various cancer conditions and neurological conditions, and precursors and sequelae thereof in humans. Particularly beneficial results are appreciated through oral administration in the prevention and treatment of familial adenomatous polyposis (FAP), as well as colon cancer and other sequelae of FAP, particularly in human subjects who are identified as being genetically predisposed to develop FAP. Particular benefits are also appreciated in reducing and preventing the progression of FAP and in preventing or delaying the need for colonic resection which is often required before the age of 25 years in humans with FAP.

Preferably, preparations according to the preferred embodiments are administered at a regular frequency, preferably at frequencies of three times per week (either on three consecutive days, or on three regularly distributed days of the week).

Although dosing may vary based on particular needs and preferred treatment protocols according to physician preference, maximum tolerable daily bioavailable dosings (trough levels) for a 28-day duration are about 200 micrograms of rapamycin (or equivalent) per subject kilogram, for both human and canine subjects, although those of ordinary skill would understand that greater dose amount ranges would be tolerable and suitable when administered less often than once per day, and lesser ranges would be tolerable when administered more often than once per day.

Whereas prior art uses of rapamycin may have involved recommended daily dosings of roughly 13 micrograms per kilogram in human subjects, oncology protocols, according to preferred embodiments of the present invention, use higher dosings than the prior art, preferably in a range of more than 50 micrograms and up to (or even exceeding) 200 micrograms per kilogram for daily administration, or the equivalent for other frequencies of administration. Other conditions addressed by oral administration protocols of the present invention include preventing and treating gingivitis in humans, dogs and cats, whether through the preferred preparations of rapamycin (or the equivalent) or through combination therapies with stem cell therapy and/or other active pharmaceutical or botanical treatment protocols.

In contrast to oncology-related dosings, preferred protocols for oral administration of the preparations taught herein when used for prevention and treatment of targeted neurological conditions, and reducing the progression thereof, use lower dosings than the prior art. Such lower dosings are preferably about 5 micrograms of bioavailable rapamycin (or the equivalent) per daily oral dose, and such dosings otherwise more generally fall in the preferred range of between 1 and 7 micrograms per kilogram for once-daily administration, or the equivalent for other frequencies of administration.

Although various neurological indications are targeted in alternative embodiments, preferred embodiments of oral administration protocols according to the present invention are used for preventing and treating, and reducing the progression of Alzheimer's disease, pre-Alzheimer's disease, vascular dementia and other variations of cognitive impairment in general in humans, canines, felines and other animal subject types. Such embodiments include preventing and treating anxiety disorders in canines and felines, as well as reducing the progression of neurological impairment in human subjects exhibiting indications related to Alzheimer's disease, vascular dementia, or precursors to onset of Alzheimer's disease.

Alternative Embodiments with Other Rapamycins

Although many aspects of the present invention relate directly to rapamycin itself, possible broader aspects of the invention relate also to analogs and derivatives of rapamycin, and to producing a more stable and effective oral preparation for delivering an agent to bind, interact with or otherwise regulate activity of the mTOR pathway.

Accordingly, as alternatives that benefit from many but not necessarily all of the teachings of the present invention, any of the particular embodiments described above may be modified by substituting one or more other rapamycins in place of (or in addition to) rapamycin. For corresponding purposes of these descriptions, all mTOR pathway inhibitors should be considered as "rapamycins" (i.e., the plural of rapamycin). Also, in this context and wherever else a context relates to any of the rapamycins rather than just rapamycin, any related references to "encapsulated rapamycin" should be read as teaching not only about discrete particles that include rapamycin, but also about discrete particles that include any one or more rapamycins.

General Alternatives

It should be understood that the foregoing disclosure emphasizes certain specific embodiments of the invention and that all substitutions, modifications or alternatives equivalent thereto should be presumed to fall within the spirit and scope of the invention. While reference is made in many respects to incorporation of various rapamycin nanoparticle embodiments, it should also be recognized that the spirit and scope of the invention may not be limited to nanoparticles as such, nor to the other particular compounds or the like referenced herein.

In all respects, it should also be understood that the drawings and detailed description herein are to be regarded in an illustrative rather than a restrictive manner, and are not intended to limit the invention to the particular forms and examples disclosed. Rather, the invention includes all embodiments and methods within the scope and spirit of the invention as claimed, as the claims may be amended, replaced or otherwise modified during the course of related prosecution. Any current, amended, or added claims should be interpreted to embrace all further modifications, changes, rearrangements, substitutions, alternatives, design choices, and embodiments that may be evident to those of skill in the art, whether now known or later discovered. In any case, all substantially equivalent systems, articles, and methods should be considered within the scope of the invention and, absent express indication otherwise, all structural or functional equivalents are anticipated to remain within the spirit and scope of the present inventive system and method.

It is also specifically contemplated that any of the particular encapsulated rapamycin embodiments described herein may be provided in daily oral doses (once or twice daily) for any of the medical or veterinary applications referenced throughout this specification or that may be referenced in US Patent Application 2012/0064143 and any other publications describing possible uses for encapsulated rapamycin.

For other alternatives, it should be understood that any limitation discussed with respect to one embodiment of the invention may apply to any other embodiment of the invention. Moreover, any composition of the invention may be used in any method of the invention, and any method of the invention may be used to produce or to utilize any composition of the invention. Any embodiment of the present invention may consist of or consist essentially of—rather than comprise/include/contain/have—the described features and/or steps.

Accordingly and otherwise, many other alternatives will be evident to those of skill in the art. Rather than being limited by the embodiment descriptions as set forth above, the invention itself should ultimately be contemplated based on any claims that may be appended hereto or added in the course of prosecuting this patent application or other patent applications that claim direct or indirect priority to this patent application. All descriptive materials referenced herein are incorporated by reference in their entirety, for all purposes.

The invention claimed is:

1. A microparticle pharmaceutical preparation, comprising:
    an enteric coating comprising a solid excipient matrix, said solid excipient matrix comprising a polymer composition that remains intact when exposed to acidic conditions of the alimentary canal of an animal and that disintegrates in near-neutral to basic conditions of targeted intestinal portions of said alimentary canal;
    said polymer comprising a copolymer of methacrylic acid and methyl methacrylate;
    rapamycin nanoparticles dispersed within said matrix, said rapamycin nanoparticles comprising a micelle-inducing compound, wherein said micelle-inducing compound comprises sodium cholate, and a pharmaceutically active core comprising said rapamycin nanoparticles; and
    said micelle-inducing compound naturally inducing formation of micelles with a solution of said micelle-inducing compound, said micelles having properties that promote stability of said rapamycin when said rapamycin nanoparticles are dispersed within said matrix; and said rapamycin nanoparticles are sized in the range between about 1 nanometer and about 1 micron.

2. A microparticle pharmaceutical preparation, comprising:

an enteric coating comprising a solid excipient matrix, said solid excipient matrix comprising a polymer composition that remains intact when exposed to acidic conditions of the alimentary canal of an animal and that disintegrates in near-neutral to basic conditions of targeted intestinal portions of said alimentary canal;

said polymer comprising a copolymer of methacrylic acid and methyl methacrylate;

rapamycin nanoparticles dispersed within said matrix, said rapamycin nanoparticles comprising a micelle-inducing compound, wherein said micelle-inducing compound comprises a surfactant, and a pharmaceutically active core comprising a rapamycin, said surfactant comprising sodium cholate;

said sodium cholate naturally inducing formation of micelles with a solution of said sodium cholate, said micelles having properties that promote stability of said rapamycin when said rapamycin nanoparticles are dispersed within said matrix; and said rapamycin nanoparticles are sized in the range between about 1 nanometer and about 1 micron.

3. The preparation of claim 2, further comprising:

a rapamycin nanoparticle dispersion of said rapamycin nanoparticles, said rapamycin nanoparticle dispersion comprising:

a rapamycin solution comprising said rapamycin dissolved in a water-miscible solvent; and said sodium cholate solution comprising said sodium cholate dissolved in a volume of deionized water.

4. The preparation of claim 3, wherein said sodium cholate is at a concentration above its critical micelle concentration.

5. The preparation of claim 2, wherein a volumetric ratio of said rapamycin solution and said sodium cholate solution is between about 1:10 to about 1:1.

6. The preparation of claim 2, wherein a volumetric ratio of said rapamycin solution and said sodium cholate solution is between about 1:5 to about 1:1.

7. The preparation of claim 2, wherein said rapamycin is dissolved in said water-miscible solvent at a concentration of between about 0.01% weight to volume to about 10% weight to volume.

8. The preparation of claim 2, wherein said water-miscible solvent comprises methanol.

9. The preparation of claim 2, wherein said rapamycin is dissolved in said water-miscible solvent at a concentration of between about 0.1% weight to volume to about 10% weight to volume.

10. A microparticle pharmaceutical preparation, comprising:

a solid matrix, said solid matrix comprising a polymer composition that remains intact when exposed to acidic conditions of the alimentary canal of an animal and that disintegrates in near-neutral to basic conditions of targeted intestinal portions of said alimentary canal;

said polymer comprising a methacrylic acid copolymer with methyl methacrylate;

rapamycin nanoparticles dispersed within said solid matrix, said rapamycin nanoparticles comprising micelles of sodium cholate and pharmaceutically active cores comprising a rapamycin, said micelles having properties that promote stability of said rapamycin when said rapamycin nanoparticles are dispersed within said solid matrix;

said rapamycin nanoparticles being sized in the range between about 1 nanometer and about 1 micron;

a solution of said sodium cholate; and a solution of said rapamycin.

11. The preparation of claim 10, wherein said methacrylic acid copolymer comprises methacrylic acid and methyl methacrylate at a comonomer ratio of 1:2.

12. The preparation of claim 10, wherein said micelles are the product of a process wherein said sodium cholate is dissolved in a volume of deionized water to form said sodium cholate solution at a concentration above its critical micelle concentration.

13. The preparation of claim 12, wherein the process for producing said rapamycin nanoparticles comprises combining said sodium cholate solution with said rapamycin solution, and wherein a volumetric ratio of said rapamycin solution and said sodium cholate solution is between about 1:10 to about 1:1.

14. The preparation of claim 13, wherein said rapamycin solution is created by dissolving said rapamycin in a water-miscible solvent at a concentration of between about 0.01% weight to volume to about 10% weight to volume.

15. A microparticle pharmaceutical preparation, comprising:

a solid matrix, comprising a polymer composition that remains intact when exposed to acidic conditions of the alimentary canal of an animal and that disintegrates in near-neutral to basic conditions of targeted intestinal portions of said alimentary canal;

said polymer comprising a copolymer of methacrylic acid and methyl methacrylate;

rapamycin nanoparticles dispersed within said matrix, said rapamycin nanoparticles comprising micelles and pharmaceutically active cores, said micelles comprising sodium cholate, and said pharmaceutically active cores comprising a rapamycin;

said micelles having properties that promote stability of said rapamycin when said rapamycin nanoparticles are dispersed within said solid matrix;

said rapamycin nanoparticles being produced by a process including the creation of a mixture of a rapamycin solution and a sodium cholate solution, wherein:

a volumetric ratio of said rapamycin solution and said sodium cholate solution is between about 1:10 to about 1:1;

said rapamycin solution comprises said rapamycin dissolved in a water-miscible solvent at a concentration of between about 0.01% to about 10%;

said water miscible-solvent comprises methanol; and said sodium cholate solution comprises said sodium cholate dissolved in a volume of deionized water, wherein said sodium cholate is at a concentration above its critical micelle concentration.

* * * * *